United States Patent [19] [11] 4,331,674
Krämer et al. [45] May 25, 1982

[54] COMBATING FUNGI WITH 4-PHENOXY-4-(AZOLYL-1-YL)-BUTANOIC ACID DERIVATIVES

[75] Inventors: Wolfgang Krämer; Jörg Stetter; Karl H. Büchel, all of Wuppertal; Paul-Ernst Frohberger, Leverkusen; Wilhelm Brandes, Cologne, all of Fed. Rep. of Germany

[73] Assignee: Bayer Aktiengesellschaft, Leverkusen, Fed. Rep. of Germany

[21] Appl. No.: 819,533

[22] Filed: Jul. 27, 1977

[30] Foreign Application Priority Data

Aug. 7, 1976 [DE] Fed. Rep. of Germany ....... 2635663

[51] Int. Cl.³ .................. A01N 43/50; A01N 43/64; C07D 233/60; C07D 249/08
[52] U.S. Cl. ............... 424/269; 260/465 D; 260/465 E; 260/465 F; 424/232; 424/273 R; 424/248.52; 424/248.56; 424/248.55; 424/248.58; 424/250; 424/267; 544/132; 544/139; 544/174; 544/366; 544/370; 546/210; 548/262; 548/341; 560/9; 560/46; 560/55; 564/162; 564/167
[58] Field of Search ................ 260/308 R; 548/341, 548/262; 424/232, 269, 273, 273 R

[56] References Cited

U.S. PATENT DOCUMENTS 3,732,242 5/1973 Buchel et al. ............... 548/341
3,812,142 5/1974 Meiser et al. ............... 548/341
3,952,002 4/1976 Kramer et al. ............... 424/269
4,005,083 1/1977 Buchel et al. ............... 260/299
4,036,966 7/1977 Meiser et al. ............... 260/308 R Primary Examiner—Alton D. Rollins Attorney, Agent, or Firm—Sprung, Horn, Kramer & Woods

[57] ABSTRACT

4-Phenoxy-4-(azolyl-1-yl)-butanoic acid derivatives of the formula

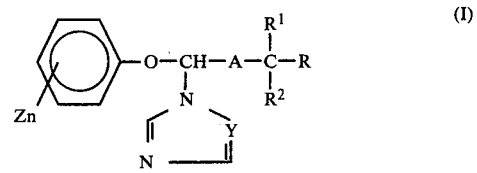

in which
A is —CO— or CH(OH)—,
Y is —CH= or —N=,
Z is halogen, alkyl, alkenyl, halogenoalkyl, cycloalkyl, alkoxy, alkylthio, alkoxycarbonyl, phenyl, phenoxy, phenylalkyl, substituted phenyl, phenoxy or phenylalkyl, amino, cyano or nitro,
R is cyano, —CO—OR³ or —CO—NR⁴R⁵,
R¹ and R² each independently is alkyl, phenyl or substituted phenyl, or conjointly form a carbocyclic ring,
R³ is alkyl,
R⁴ is hydrogen, alkyl, phenyl or substituted phenyl and
R⁵ is hydrogen or alkyl, or
R⁴ and R⁵ conjointly form a methylene bridge —(CH₂)$_m$— which can contain a further heteroatom,
m is 2, 3, 4, 5, 6 or 7,
n is 0, 1, 2, 3, 4 or 5,
and salts thereof, which possess fungicidal properties.

10 Claims, No Drawings

COMBATING FUNGI WITH 4-PHENOXY-4-(AZOLYL-1-YL)-BUTANOIC ACID DERIVATIVES

The present invention relates to and has for its objects the provision of particular new 4-phenoxy-4-(azolyl-1-yl)-butanoic acid derivatives which possess properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has been disclosed in U.S. Pat. Nos. 3,898,341, 3,912,752, 3,940,414 and 3,952,002 that 1-(imidazol-1-yl)-3,3-dimethyl-1-phenoxy-butan-2-ones and -ols, and 3,3-dimethyl-1-phenoxy-1-(1,2,4-triazol-1-yl)-butan-2-ones and -ols, especially when substituted in the phenoxy part, possess a good fungicidal activity. However, their action is not always entirely satisfactory, especially when low amounts and low concentrations are used.

The present invention now provides, as new compounds, the azolyl-carboxylic acid derivatives of the general formula

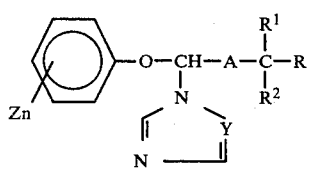

in which
A is —CO— or CH(OH)—,
Y is —CH= or —N=,
Z is halogen, alkyl, alkenyl, halogenoalkyl, cycloalkyl, alkoxy, alkylthio, alkoxycarbonyl, phenyl, phenoxy, phenylalkyl, substituted phenyl, phenoxy or phenylalkyl, amino, cyano or nitro,
R is cyano, —CO—OR$^3$ or —CO—NR$^4$R$^5$,
R$^1$ and R$^2$ each independently is alkyl, phenyl or substituted phenyl, or conjointly form a carbocyclic ring,
R$^3$ is alkyl,
R$^4$ is hydrogen, alkyl, phenyl or substituted phenyl and
R$^5$ is hydrogen or alkyl, or
R$^4$ and R$^5$ conjointly form a methylene bridge —(CH$_2$)$_m$— which can contain a further heteroatom,
m is 2, 3, 4, 5, 6 or 7,
n is 0, 1, 2, 3, 4 or 5,
and their salts.

Surprisingly, the active compounds according to the invention exhibit a substantially higher fungicidal activity, especially against cereal diseases, than the 1-(imidazol-1-yl)-3,3-dimethyl-1-phenoxy-butan-2-ones or -ols and 3,3-dimethyl-1-phenoxy-1-(1,2,4-triazol-1-yl)butan-2-ones or -ols known from the state of the art, which are chemically, and in respect of their action, closely related compounds, The active compounds according to the invention thus represent an enrichment of the art.

Preferably, R represents cyano or a —CO—OR$^3$ or —CO—NR$^4$R$^5$ grouping, wherein R$^3$ represents straight-chain or branched alkyl with 1 to 6 carbon atoms, R$^4$ represents hydrogen, straight-chain or branched alkyl with 1 to 4 carbon atoms or phenyl which is optionally substituted by halogen (especially fluorine, chlorine or bromine), alkyl with 1 or 2 carbon atoms or halogenoalkyl with 1 or 2 carbon atoms and 1 to 5 halogen atoms (especially fluorine and chlorine atoms, the trifluoromethyl group being an example) and R$^5$ represents hydrogen or straight-chain or branched alkyl with 1 to 4 carbon atoms or R$^4$ and R$^5$ conjointly represent a 5-membered or 6-membered ring which can contain, as a further hetero-atom, oxygen or nitrogen (examples being pyrrolidine, piperidine, piperazine and morpholine);

R$^1$ and R$^2$, which may be identical or different, each represent alkyl with 1 to 4 carbon atoms or phenyl which is optionally substituted by halogen (especially fluorine, chlorine or bromine), alkyl with 1 or 2 carbon atoms or halogenoalkyl with 1 or 2 carbon atoms and 1 to 5 halogen atoms (especially fluorine and chlorine atoms, the trifluoromethyl group being an example) or R$^1$ and R$^2$ conjointly represent a 5-membered or 6-membered carbocyclic ring;

Z represents halogen, straight-chain or branched alkyl with 1 to 4 carbon atoms, alkenyl with 2 to 4 carbon atoms, cycloalkyl with 5 to 7 carbon atoms (preferably cyclohexyl), halogenoalkyl with 1 or 2 carbon atoms and 1 to 5 halogen atoms (especially fluorine and chlorine atoms, the trifluoromethyl group being an example), alkoxy with 1 or 2 carbon atoms, alkylthio with 1 or 2 carbon atoms, alkoxycarbonyl with 1 to 5 carbon atoms in the alkoxy part, amino, cyano, nitro or phenyl or phenoxy, either of which may be substituted by halogen, amino, cyano, nitro or alkyl with 1 or 2 carbon atoms, or Z represents phenylalkyl with 1 or 2 carbon atoms in the alkyl part and which may be substituted in the alkyl part by alkylcarbonyl with a total of up to 3 carbon atoms and/or in the phenyl part by halogen (namely fluorine, chlorine, bromine or iodine), nitro or cyano;

and n represents 0, 1, 2 or 3.

Those compounds of the formula (I) in which A represents the CH(OH) group possess two asymmetric carbon atoms and can therefore exist as the two geometrical isomers (erythro form the threo form), which may be formed in different ratios. In both cases, the geometrical isomers exist as optical isomers. All the isomers are intended to be covered by the above formula (I).

Furthermore, the azolyl-carboxylic acid derivatives obtainable according to the invention can be converted to the salts by reaction with acids. Conversely, the acid addition salts can be converted back into the free bases by treatment with suitable bases.

From the point of view of phytotoxicity, preferred salts of the compounds of the formula (I) are physiologically tolerated salts, these being generally salts of physiologically tolerated acids. The preferred acids include the hydrogen halide acids (for example hydrobromic acid and especially hydrochloric acid), phosphoric acid, nitric acid, monofunctional and bifunctional carboxylic acids and hydroxycarboxylic acids (for example acetic acid, maleic acid, succinic acid, fumaric acid, tartaric acid, salicylic acid, citric acid, sorbic acid and lactic acid) and 1,5-naphthalenedisulphonic acid.

The present invention also provides a process for the preparation of an azolyl-carboxylic acid derivative of the formula (I), in which a bromo-ketocarboxylic acid derivative of the general formula

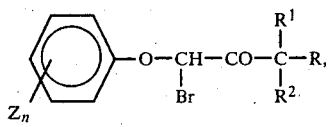

in which

R, $R^1$, $R^2$, Z and n have the above-mentioned meanings, is reacted with an azole of the general formula

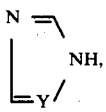

in which Y has the above-mentioned meaning, in the presence of a diluent and of an acid-binding agent and, if appropriate, the azolyl-keto-carboxylic acid derivative thereby obtained is reduced selectively, in a manner which is in itself known, by means of a complex borohydride, if appropriate in the presence of a diluent.

If 4-bromo-4-(4-chlorophenoxy)-2,2-dimethyl-3-ketobutanoic acid ethyl ester and 1,2,4-triazole are used as starting materials, the course of the reaction can be represented by the following equation:

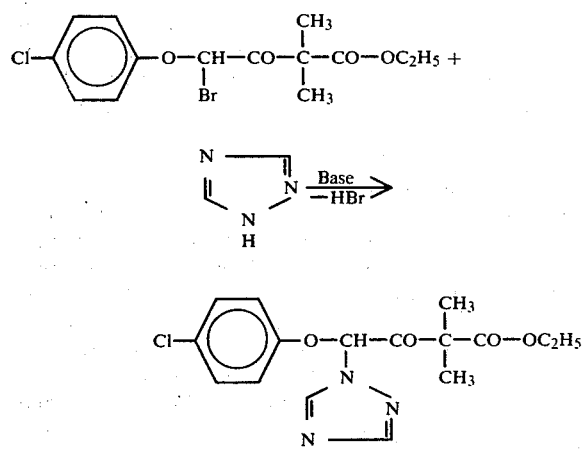

If 4-(4-chlorophenoxy)-2,2-dimethyl-3-keto-4-(1,2,4-triazol-1-yl)-butanoic acid ethyl ester and sodium borohydride are used as starting materials, the course of the reaction can be represented by the following equation:

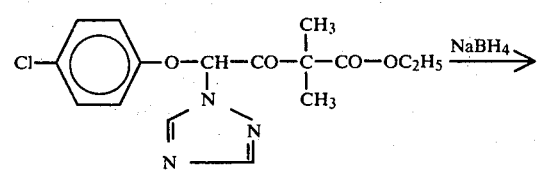

-continued

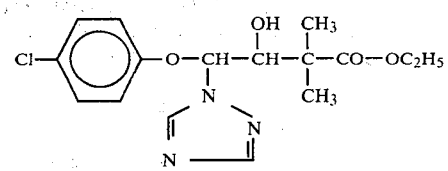

The following may be mentioned as examples of starting materials of the general formula (II): 4-bromo-4-(4-chlorophenoxy)-2,2-dimethyl-3-keto-butanoic acid ethyl ester, 4-bromo-4-(2,4-dichlorophenoxy)-2,2-dimethyl-3-keto-butanoic acid ethyl ester, 4-bromo-4-(4-fluorophenoxy)-2,2-dimethyl-3-keto-butanoic acid ethyl ester, 4-bromo-4-(4-bromophenoxy)-2,2-dimethyl-3-keto-butanoic acid ethyl ester, 4-bromo-4-(2,4,5-trichlorophenoxy)-2,2-dimethyl-3-keto-butanoic acid ethyl ester, 4-bromo-4-(2-methylphenoxy)-2,2-dimethyl-3-ketobutanoic acid ethyl ester, 4-bromo-4-(3,4-dimethylphenoxy)-2,2-dimethyl-3-keto-butanoic acid ethyl ester, 4-bromo-4-(4-chloro-3,5-dimethylphenoxy)-2,2-dimethyl-3-keto-butanoic acid ethyl ester, 4-bromo-4-(2-cyclohexylphenoxy)-2,2-dimethyl-3-keto-butanoic acid ethyl ester, 4-bromo-4-(4-methoxyphenoxy)-2,2-dimethyl-3-keto-butanoic acid ethyl ester, 4-bromo-4-(3-trifluoromethylphenoxy)-2,2-dimethyl-3-ketobutanoic acid ethyl ester, 4-bromo-4-(2-phenylphenoxy)-2,2-dimethyl-3-keto-butanoic acid ethyl ester, 4-bromo-4-(4-phenylphenoxy)-2,2-dimethyl-3-ketobutanoic acid ethyl ester, 4-bromo-4-[4-(4'-chlorophenoxy)-phenoxy]-2,2-dimethyl-3-ketobutanoic acid ethyl ester, 4-bromo-4-[4-(4'-chlorobenzyl)phenoxy]-2,2-dimethyl-3-keto-butanoic acid ethyl ester, 4-bromo-4-(4-cyanophenoxy)-2,2-dimethyl-3-keto-butanoic acid ethyl ester, 4-bromo-4-(4-nitrophenoxy)-2,2-dimethyl-3-ketobutanoic acid ethyl ester, 4-bromo-4-[4-(4'-chlorophenyl)phenoxy]-2,2-dimethyl-3-keto-butanoic acid ethyl ester, 4-bromo-4-(2-methyl-5-nitrophenoxy)-2,2-dimethyl-3-ketobutanoic acid ethyl ester, 4-bromo-4-(4-chlorophenoxy)-2,2-dimethyl-3-keto-butanoic acid methyl ester, 4-bromo-4-(4-chlorophenoxy)-2,2-dimethyl-3-keto-butanoic acid propyl ester, 4-bromo-4-(4-chlorophenoxy)-2,2-dimethyl-3-ketobutanoic acid iso-propyl ester, 4-bromo-4-(4-chlorophenoxy)-2,2-dimethyl-3-keto-butanoic acid tert.-butyl ester, 4-bromo-4-(4-chlorophenoxy)-2,2-dimethyl-3-keto-butanoic acid amide, 4-bromo-4-(4-chlorophenoxy)-2,2-dimethyl-3-ketobutanoic acid methylamide, 4-bromo-4-(4-chlorophenoxy)-2,2-dimethyl-3-keto-butanoic acid dimethylamide, 4-bromo-4-(4-chlorophenoxy)-2,2-dimethyl-3-keto-butanoic acid phenylamide, 4-bromo-4-(4-chlorophenoxy)-2,2-dimethyl-3-keto-butanoic acid 4-chlorophenylamide, 4-bromo-4-(4-chlorophenoxy)-2,2-dimethyl-3-keto-butanoic acid morpholide, 2-ethyl-4-bromo-4-(4-chlorophenoxy)-3-keto-2-methyl-butanoic acid ethyl ester, 4-bromo-4-(4-chlorophenoxy)-3-keto-2-methyl-2-propylbutanoic acid ethyl ester, 4-bromo-4-(4-chlorophenoxy)-2-iso-propyl-3-keto-2-methyl-butanoic acid ethyl ester, 4-bromo-4-(4-chlorophenoxy)-3-keto-2,2-pentamethylene-butanoic acid ethyl ester, 4-bromo-4-(4-chlorophenoxy)-3-keto-2-methyl-2-phenyl-butanoic acid ethyl ester, 4-bromo-4-(4-chlorophenoxy)-2-(4-chlorophenyl)-3-keto-2-methyl-butanoic acid ethyl ester and 4-bromo-4-(4-chlorophenoxy)-2-(2,4-dichlorophenyl)-3-keto-2-methyl-butanoic acid ethyl ester.

The bromo-keto-carboxylic acid derivatives of the formula (II) to be used as starting materials can be prepared in accordance with known processes, for example by reacting known phenols of the general formula

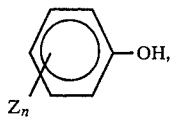

in which Z and n have the above-mentioned meanings, with known bromo ketones of the general formula

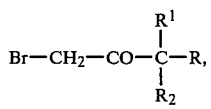

in which R, $R^1$ and $R^2$ have the above-mentioned meanings.

The active hydrogen atom which still remains is subsequently replaced by bromine in the usual manner, as shown in the preparative examples hereinbelow.

The azoles of the formula (III) are well known compounds.

Preferred diluents for the reaction according to the invention are inert organic solvents, especially ketones, such as diethyl ketone and especially acetone and methyl ethyl ketone; nitriles, such as propionitrile and especially acetonitrile; alcohols, such as ethanol or isopropanol; ethers, such as tetrahydrofuran or dioxane; benzene; formamides, such as, in particular, dimethylformamide; and halogenated hydrocarbons, such as methylene chloride, carbon tetrachloride or chloroform.

The reaction is carried out in the presence of an acid-binding agent. All inorganic or organic acid-binding agents which can usually be employed may be added, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylmethylamine, N,N-dimethylbenzylamine and also pyridine and diazabicyclooctane. Furthermore, an appropriate excess of the azole (III) may be used.

The reaction temperatures can be varied within a substantial range. In general, the reaction is carried out at from 20° to 150° C., preferably at 60° to 120° C. In the presence of a solvent, the reaction is advantageously carried out at the boiling point of the particular solvent.

In carrying out the process according to the invention, preferably 1 to 2 moles of azole and 1 to 2 moles of acid-binding agent are employed per mole of the compounds of the formula (II). To isolate the compounds of the formula (I), the solvent is distilled off, the residue is taken up in an organic solvent and the solution is washed with water. The organic phase is dried over sodium sulphate and freed from the solvent in vacuo. The residue is purified by distillation or recrystallization.

In the reaction according to the invention, polar organic solvents may be used as diluents for the selective reduction, preferably alcohols, such as methanol, ethanol, butanol and isopropanol, and ethers, such as diethyl ether or tetrahydrofuran. The reduction reaction is in general carried out at from 0° to 30° C., preferably at 0° to 20° C. For this reaction, 1 mole of a borohydride, such as sodium borohydride, is preferably employed per mole of the compound of the formula (II). To isolate the compounds of the formula (I), the residue is taken up in, for example, dilute hydrochloric acid and the solution is then rendered alkaline and extracted with an organic solvent, or the residue is merely mixed with water and extracted by shaking with an organic solvent. The further working up takes place in the usual manner.

The following may be mentioned, by way of example, as active compounds according to the invention that are particularly active: 4-(4-chlorophenoxy)-3-keto-2-methyl-2-phenyl-4-(1,2,4-triazol-1-yl)-butanoic acid ethyl ester, 2-ethyl-4-(4-chlorophenoxy)-3-keto-2-methyl-4-(1,2,4-triazol-1-yl)-butanoic acid ethyl ester, 2-ethyl-4-(4-chlorophenoxy)-4-(imidazol-1-yl)-3-keto-2-methyl-butanoic acid ethyl ester, 4-(4-chlorophenoxy)-3-keto-2-methyl-2-propyl-4-(1,2,4-triazol-1-yl)-butanoic acid ethyl ester, 4-(4-chlorophenoxy)-2-iso-propyl-3-keto-2-methyl-4-(1,2,4-triazol-1-yl)-butanoic acid ethyl ester, 4-(4-chlorophenoxy)-2-iso-propyl-4-(imidaziol-1-yl)-3-keto-2-methyl-butanoic acid ethyl ester, 4-(4-chlorophenoxy)-2,2-diethyl-3-keto-4-(1,2,4-triazol-1-yl)-butanoic acid ethyl ester, 4-(4-chlorophenoxy)-2,2-diethyl-4-(imidazol-1-yl)-3-keto-butanoic acid ethyl ester, 2-butyl-4-(4-chlorophenoxy)-3-keto-2-methyl-4-(1,2,4-triazol-1-yl)-butanoic acid ethyl ester, 2-butyl-4-(4-chlorophenoxy)-4-(imidazol-1-yl)-3-keto-2-methyl-butanoic acid ethyl ester, 4-(4-chlorophenoxy)-3-keto-2,2-pentamethylene-4-(1,2,4-triazol-1-yl)-butanoic acid ethyl ester, 4-(4-chlorophenoxy)-2,2-dimethyl-3-keto-4-(1,2,4-triazol-1-yl)-butanoic acid 4-chlorophenylamide, 2-butyl-4-(4-chlorophenoxy)-2-iso-propyl-3-keto-4-(1,2,4-triazol-1-yl)-butanoic acid phenylamide, 2-butyl-4-(4-chlorophenoxy)-4-(imidazol-1-yl)-2-iso-propyl-3-keto-butanoic acid phenylamide, 4-(4-chlorophenoxy)-2,2-dimethyl-3-keto-4-(1,2,4-triazol-1-yl)-butanoic acid dimethylamide, 4-(4-biphenylyloxy)-2,2-dimethyl-3-keto-4-(1,2,4-triazol-1-yl)-butanoic acid ethyl ester, 4-(4-biphenylyloxy)-2,2-dimethyl-4-(imidazol-1-yl-3-keto-butanoic acid ethyl ester, [4-(4-chlorophenyl)-phenoxy]-2,2-dimethyl-3-keto-4-(1,2,4-triazol-1-yl)-butanoic acid ethyl ester, [4-(4-chlorophenyl)-phenoxy]-2,2-dimethyl-4-(imidazol-1-yl)-3-keto-butanoic acid ethyl ester, 2,2-dimethyl-3-keto-4-(4-nitrophenoxy)-4-(1,2,4-triazol-1-yl)-butanoic acid ethyl ester, 2,2-dimethyl-4-(imidazol-1-yl)-3-keto-4-(4-nitrophenoxy)-butanoic acid ethyl ester, 4-(4-chloro-2-methylphenoxy)-2,2-dimethyl-3-keto-4-(1,2,4-triazol-1-yl)-butanoic acid ethyl ester, 4-(4-chloro-2-methylphenoxy)-2,2-dimethyl-4-(imidazol-1-yl)-3-keto-butanoic acid ethyl ester, 4-(2,4-dichlorophenoxy)-2,2-dimethyl-3-keto-4-(1,2,4-triazol-1-yl)-butanoic acid ethyl ester, 4-(2,4-dichlorophenoxy)-2,2-dimethyl-4-(imidazol-1-yl)-3-keto butanoic acid ethyl ester, 4-(4-bromophenoxy)-2,2-dimethyl-3-keto-4-(1,2,4-triazol-1-yl)-butanoic acid ethyl ester, 4-(4-bromophenoxy)-2,2-dimethyl-4-(imidazol-1-yl)-3-keto butanoic acid ethyl ester, 2,2-dimethyl-4-(4-fluorophenoxy)-3-keto-4-(1,2,4-triazol-1-yl)-butanoic acid ethyl ester, 2,2-dimethyl-4-(4-fluorophenoxy)-4-(imidazol-1-yl)-3-keto-butanoic acid ethyl ester, 4-(4-chlorophenoxy)-2,2-dimethyl-3-keto-4-(1,2,4-triazol-1-yl)-butanoic acid tert.-butyl ester, 4-(4-chlorophenoxy)-2,2-dimethyl-4-(imidazol-1-yl)-3-keto butanoic acid tert.-butyl ester, 2-butyl-4-(4-chlorophenoxy)-2-isopropyl-3-keto-4-(1,2,4-triazol-1-yl)-butanoic acid ethyl ester, 2-butyl-4-(4-chlorophenoxy)-4-(imidazol-1-yl)-2- isopropyl-3-keto-butanoic acid ethyl ester, 2-ethyl-2-butyl-4-(4-chlorophenoxy)-3-keto-4-(1,2,4-triazol-1-yl)-butanoic acid ethyl ester and 2-ethyl-2-butyl-4-(4-chlorophenoxy)-4-(imidazol-1-yl)-3-keto-butanoic acid ethyl ester.

The active compounds according to the invention exhibit a powerful fungitoxic action and a bacteriotoxic action. They do not damage crop plants in the concentrations required for combating fungi and bacteria. For these reasons they are suitable for use as plant protection agents for combating fungi and bacteria. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or attack the plants through the soil, and also against seed-borne pathogens.

They develop a particularly good activity against parasitic fungi on above-ground parts of plants, such as species of Erysiphe, species of Uromyces and species of Venturia, and also species of Pyricularia and species of Pellicularia. Good actions are achieved against the pathogen of apple scab (*Fusicladium dendriticum*), of bean rust (*Uromyces phaseoli*) and of powdery mildew of cucumbers (*Erysiphe cichoriacearum*), and also against the fungus *Pellicularia sasakii*. Furthermore, the compounds display a high activity against cereal diseases, such as cereal mildew, cereal rust and loose smuts of barley. An aspect to be singled out particularly is that the active compounds according to the invention not only display a protective action but are also curatively active, that is to say are active when used after infection has taken place. Furthermore, the systemic action of the compounds should be pointed out. Thus it proves possible to protect plants against fungal attack by supplying the active compound to the above-ground parts of the plant through the soil and the root, or through the seed.

As plant protection agents, the compounds according to the invention can be used for the treatment of soil, for the treatment of seed and for the treatment of above-ground parts of plants.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as dichlorodifluoromethane and trichlorofluoromethane; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amines (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydolyzates, etc., and especially alkyl ar polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, nematocides, or fungicides, bactericides, rodenticides, herbicides, fertilizers, growth-regulating agents, bird repellents, growth factors, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially when used as leaf fungicides, the active compound concentrations in the use forms can be varied within a substantial range. They are, in general, from 0.1 to 0.00001 percent by weight, preferably 0.05 to 0.0001 percent.

For the treatment of seed, amounts of active compound of 0.001 to 50 g per kilogram of seed, preferably 0.01 to 10 g, are generally employed.

For the treatment of soil, amounts of active compound of 1 to 1,000 g per cubic meter of soil, preferably of 10 to 200 g, are generally employed.

When used in appropriate amounts, the compounds according to the invention also exhibit a growth-regulating activity.

Furthermore, the present invention contemplates methods of selectively killing, combatting or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

PREPARATION OF THE STARTING MATERIAL

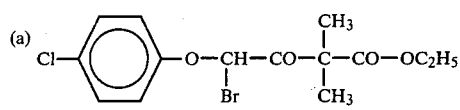

316 g (2 mol) of 4-bromo-2,2-dimethyl-3-keto-butanoic acid ethyl ester were added dropwise, at 30° C., to 246 g (2 mol) of 4-chlorophenol and 210 g of potassium carbonate in 1,000 ml of dimethylformamide. The mixture was stirred for 20 hours at room temperature and 2 hours at 40° C. The reaction mixture was then introduced into 2,000 ml of water. The aqueous phase was extracted by shaking twice with 500 ml of methylene chloride at a time and the organic phase was extracted by shaking twice with 250 ml of water each time. The combined organic phases were dried, concentrated and distilled. 324 g (56% of theory) of 4-(4-chlorophenoxy)-2,2-dimethyl-3-keto-butanoic acid ethyl ester of melting point 125–135° C./0.1 mm Hg were obtained.

26 g (0.091 mol) of 4-(4-chlorophenoxy)-2,2-dimethyl-3-keto-butanoic acid ethyl ester were dissolved in 150 ml of carbon tetrachloride. 4.7 ml (0.091 mol) of bromine in 50 ml of carbon tetrachloride were added dropwise at room temperature at such a rate that the bromine was steadily consumed. The mixture was then stirred for 30 minutes at room temperature. After distilling off the solvent in vacuo, 4-bromo-4-(4-chlorophenoxy)-2,2-dimethyl-3-keto-butanoic acid ethyl ester was obtained quantitatively and could directly be reacted further.

EXAMPLE 1

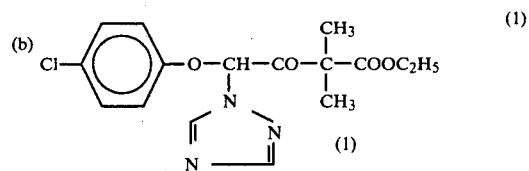

34 g (0.091 mol) of 4-bromo-4-(4-chlorophenoxy)-2,2-dimethyl-3-keto-butanoic acid ethyl ester were dissolved in 240 ml of acetonitrile. 24 g (0.345 mol) of 1,2,4-triazole were added and the mixture was heated for 48 hours under reflux. The solvent was then distilled off in vacuo, the residue was dissolved in 200 ml of methylene chloride and the solution was washed three times with 50 ml of water each time, dried over sodium sulphate and concentrated. The oil which remained was boiled up with 100 ml of petroleum ether, whereupon it crystallized. The solid was filtered off and dried. 24.9 g (78% of theory) of 4-(4-chlorophenoxy)-2,2-dimethyl-3-keto-4-(1,2,4-triazol-1-yl)-butanoic acid ethyl ester of melting point 88°–89° C. were obtained.

EXAMPLE 2

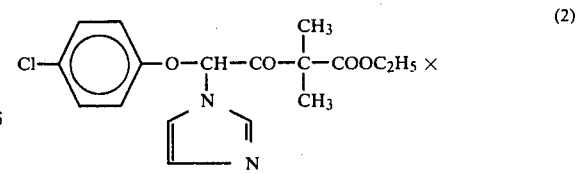

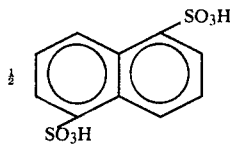

145 g (0.4 mol) of 4-bromo-4-(4-chlorophenoxy)-2,2-dimethyl-3-keto-butanoic acid ethyl ester were dissolved in 800 ml of acetonitrile. 100 g (1.45 mol) of imidazole were added and the mixture was heated for 20 hours under reflux. The solvent was then distilled off in vacuo, the residue was taken up in 500 ml of methylene chloride and the solution was washed three times with 200 ml of water each time, dried over sodium sulphate and concentrated. The oil which remained was dissolved in 800 ml of acetone and 100 g (0.35 mol) of 1,5-naphthalenedisulphonic acid in 300 ml of acetone were added. The resulting crystalline precipitate was filtered off and dried. 122.5 g (62% of theory) of 4-(4-chlorophenoxy)-2,2-dimethyl-4-(imidazol-1-yl)-3-keto-butanoic acid ethyl ester 1,5-naphthalenedisulphonate of melting point 194° C. were obtained.

EXAMPLE 3

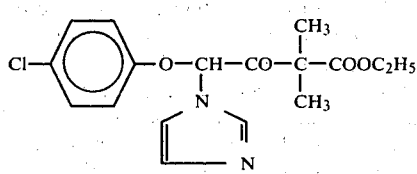

(3)

B 122.5 g (0.248 mol) of 4-(4-chlorophenoxy)-2,2-dimethyl-4-(imidazol-1-yl)-3-keto-butanoic acid ethyl ester 1,5-naphthalenedisulphonate (see Example 2) were suspended in 500 ml of methylene chloride and the suspension was stirred with 1,000 ml of saturated sodium bicarbonate solution for 0.5 hour. The organic phase was separated off, dried over sodium sulphate and concentrated. The residue crystallized on heating with 200 ml of petroleum ether. 85 g (98% of theory) of 4-(4-chlorophenoxy)-2,2-dimethyl-4-(imidazol-1-yl)-3-keto-butanoic acid ethyl ester of melting point 88° C. were obtained.

EXAMPLE 4

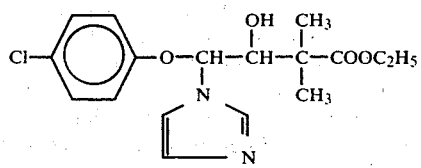

(4)

17.5 g (0.05 mol) of 4-(4-chlorophenoxy)-2,2-dimethyl-4-(imidazol-1-yl)-3-keto-butanoic acid ethyl ester (see Example 3) were dissolved in 100 ml of ethanol. 2 g (0.05 mol) of sodium borohydride were added incrementally at 0° to 10° C. and the mixture was stirred for a further 15 hours at room temperature. The solvent was then distilled off in vacuo and the residue was mixed with 100 ml of methylene chloride, 100 ml of water and 5 ml of concentrated hydrochloric acid. This mixture was stirred for 4 hours at room temperature and was neutralized with sodium bicarbonate, and the organic phase was separated off, dried over sodium sulphate and concentrated. The oily residue was recrystalized from ether/petroleum ether. 12.3 g (70% of theory) of 4-(4-chlorophenyl)-2,2-dimethyl-3-hydroxy-4-(imidazol-1-yl)-butanoic acid ethyl ester were obtained as an isomer mixture (erythro form and threo form) of melting point 120°–124° C.

EXAMPLE 5

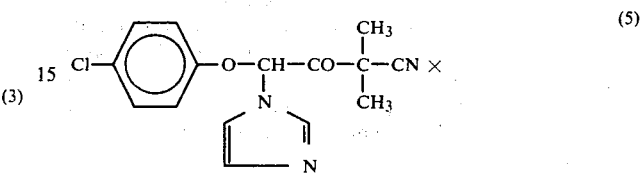

(5)

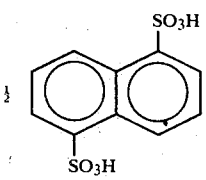

8.2 g (0.026 mol) of 1-bromo-1-(4-chlorophenoxy)-3-cyano-3-methyl-butan-2-one were dissolved in 20 ml of acetone and the solution was slowly added dropwise to a boiling mixture of 6.8 g (0.1 mol) of imidazole in 150 ml of acetone. After heating for 2 hours under reflux, the solvent was distilled off and the oily residue was partitioned in a 2-phase system of water and methylene chloride. The methylene chloride phase was separated off, repeatedly washed with water, dried over sodium sulphate and concentrated. The oily residue was taken up in 50 ml of acetone and excess 1,5-naphthalenedisulphonic acid was added. The resulting crystalline precipitate was filtered off and dried. 8 g (69% of theory) of 1-(4-chlorophenoxy)-3-cyano-1-(imidazol-1-yl)-3-methyl-butan-2-one 1,5-naphthalenedisulphonate of melting point 245° C. (with decomposition) were obtained.

The following compounds of the general formula

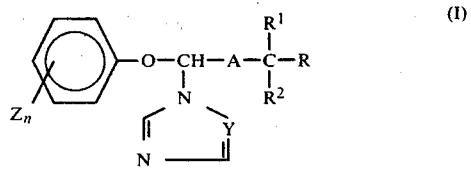

(I)

were obtained analogously to the above examples:

TABLE 1

| Compound No. | $Z_n$ | Y | A | $R^1$ | $R^2$ | R | Melting point (°C.) |
|---|---|---|---|---|---|---|---|
| 6 | 2,4-Cl$_2$ | CH | CO | CH$_3$ | CH$_3$ | —CO—OC$_2$H$_5$ | 235–237 (× ½ naphthalenedisulfonate) |
| 7 | 4-Cl | N | CO | CH$_3$ | CH$_3$ | —CO—OC$_2$H$_5$ | 128–130 (× HCl) |
| 8 | 4-Cl | N | CO | CH$_3$ | CH$_3$ | —CO—OCH$_3$ | 94–95 |
| 9 | 4-Cl | N | CO | CH$_3$ | C$_2$H$_5$ | —CO—OC$_2$H$_5$ | 91–94 |
| 10 | 4-Cl | N | CO | CH$_3$ | i-C$_3$H$_7$ | —CO—OC$_2$H$_5$ | 73–77 (decomp.) |
| 11 | 4-C$_6$H$_5$ | N | CO | CH$_3$ | CH$_3$ | —CO—OC$_2$H$_5$ | 95–97 |

TABLE 1-continued

| Compound No. | $Z_n$ | Y | A | $R^1$ | $R^2$ | R | Melting point (°C.) |
|---|---|---|---|---|---|---|---|
| 12 | 4-⟨phenyl⟩ | N | CO | $CH_3$ | $CH_3$ | $-CO-OC_2H_5$ | 72–79 (× HCl) |
| 13 | 4-Cl | CH | CO | $CH_3$ | $i-C_3H_7$ | $-CO-OC_2H_5$ | 84–88 |
| 14 | 4-Cl | N | CO | $C_2H_5$ | $C_2H_5$ | $-CO-OC_2H_5$ | 83–85 |
| 15 | 4-Cl | N | CH(OH) | $CH_3$ | $C_2H_5$ | $-CO-OC_2H_5$ | 98–102 |
| 16 | 4-Cl | CH | CO | $CH_3$ | $C_2H_5$ | $-CO-OC_2H_5$ | 86–89 |
| 17 | 4-⟨phenyl⟩ | CH | CO | $CH_3$ | $CH_3$ | $-CO-OC_2H_5$ | 83–86 |
| 18 | 4-$NO_2$ | N | CO | $CH_3$ | $CH_3$ | $-CO-OC_2H_5$ | 158 (× $HNO_3$) |

The biological activity of the novel compounds can be seen in the following examples wherein the known comparison compounds have the following structures:

(A) =
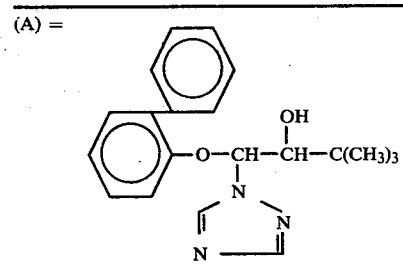

(B) =
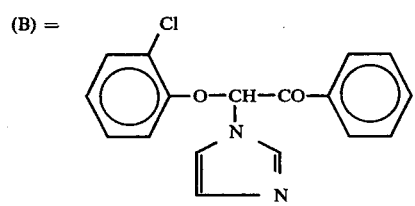

(C) =
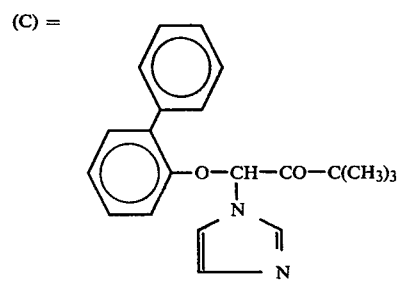

(D) =
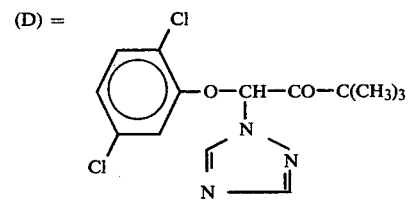

(E) =
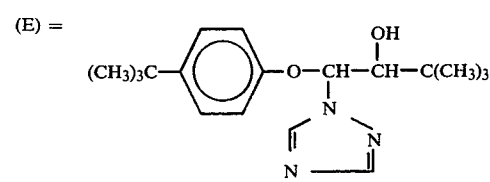

(F) =
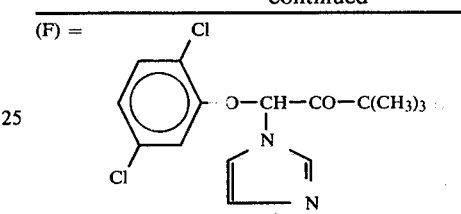

(G) =
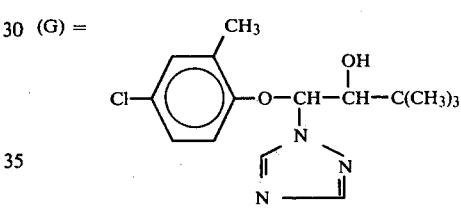

(H) =
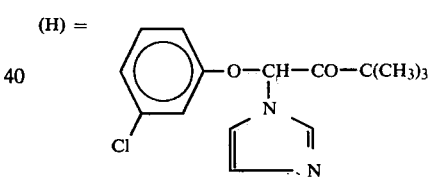

(J) =
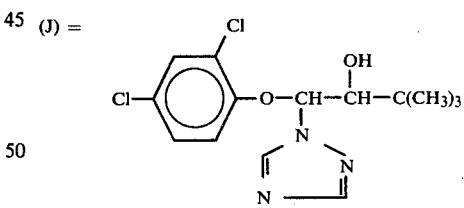

(K) =
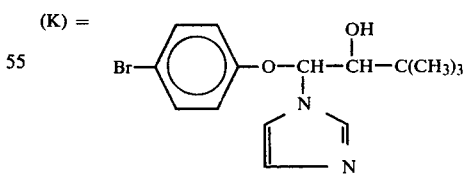

(L) =
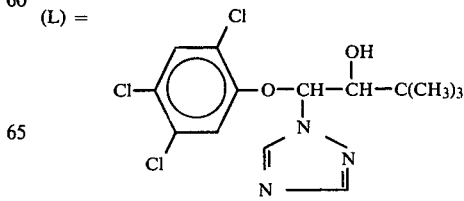

-continued

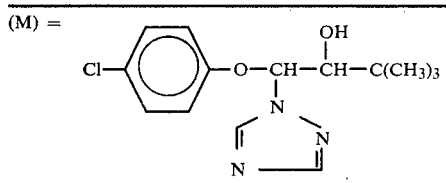

EXAMPLE 6

Shoot treatment test/cereal mildew/protective and curative (leaf-destructive mycosis)

To produce a suitable preparation of active compound, 0.25 part by weight of active compound was taken up in 25 parts by weight of dimethylformamide and 0.06 part by weight of alkylaryl polyglycol ether; 975 parts by weight of water was then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. hordei.

To test for curative activity the corresponding procedure was followed in converse sequence. The treatment of the single-leaved young barley plants with the preparation of active compound was carried out 48 hours after inoculation, when the infection was already manifest.

After 6 days' dwell time of the plants at a temperature of 21°-22° C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The active compound was the more active, the lower was the degree of mildew infection.

The active compounds, active compound concentrations in the spray liquor and degrees of infection can be seen from the table which follows:

TABLE 2

| Active compounds | Shoot treatment test/cereal mildew/ protective/curative | | |
|---|---|---|---|
| | Active compound concentration in the spray liquor in % by weight | Infection in % of the untreated control | |
| | | protective | curative |
| Untreated | — | 100.0 | 100.0 |
| (A) | 0.01 | 21.3 | 45.0 |
| (B) | 0.01 | 26.3 | — |
| (C) | 0.01 | — | 33.8 |
| (D) | 0.01 | 20.0 | — |
| (1) | 0.01 | 0.0 | 0.0 |
| (7) | 0.01 | 0.0 | 0.0 |
| (8) | 0.01 | 0.0 | — |
| (2) | 0.01 | 0.0 | — |
| (3) | 0.01 | 0.0 | — |
| (4) | 0.01 | 0.0 | — |

EXAMPLE 7

Powdery mildew of barley (*Erysiphe graminis* var. hordei)/systemic (fungal disease of cereal shoots)

The active compounds were used as pulverulent seed treatment agents. They were prepared by extending the particular active compound with a mixture of equal parts by weight of talc and kieselguhr to give a finely pulverulent mixture of the desired concentration of active compound.

For the treatment of seed, barley seed was shaken with the mixture of active compound and extender in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis* var. hordei and grown on at 21°-22° C. and 80-90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

The active compounds and concentrations of active compound in the seed treatment agent, as well as the amount used of the latter, and the percentage infection with mildew can be seen from the table which follows:

TABLE 3

| Active compounds | Barley mildew test (*Erysiphe graminis* var. horde)/systemic | | |
|---|---|---|---|
| | Active compound concentration in the dressing in % by weight | Amount of dressing used in g/kg of seed | Infection in % of the untreated control |
| Without dressing | — | — | 100.0 |
| (E) | 25 | 10 | 100.0 |
| (F) | 25 | 10 | 100.0 |
| (1) | 25 | 10 | 0.0 |
| (2) | 25 | 10 | 8.8 |
| (3) | 25 | 10 | 33.8 |
| (4) | 25 | 10 | 0.0 |

EXAMPLE 8

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80-90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The more active the compound, the lower was the degree of rust infection.

The active compounds, active compound concentrations in the spray liquor and degrees of infection can be seen from the table which follows:

TABLE 4

Shoot treatment test/cereal rust/protective

| Active compounds | Active compound concentration in the spray liquor in % by weight | Infection in % of the untreated control |
|---|---|---|
| Untreated | — | 100.0 |
| (G) | 0.025 | 82.5 |
|  | 0.01 | 100.0 |
| (H) | 0.025 | 100.0 |
| (2) | 0.025 | 25.0 |
| (3) | 0.025 | 25.0 |
| (6) | 0.01 | 12.5 |

EXAMPLE 9

Seed dressing test/loose smut of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infested with loose smut (*Ustilago nuda*), was shaken with the dressing in a closed glass flask. Two batches of 100 grains of the seed were sown 2 cm deep in seed boxes containing a mixture of 1 part by volume of Fruhstorfer standard soil and 1 part by volume of quartz sand. The boxes were placed in a greenhouse at a temperature of about 18° C., kept normally moist and exposed to light for 16 hours daily. After 10–12 weeks, the barley flowered and showed healthy panicles and diseased (smutted) panicles.

After this time, the number of diseased panicles was determined as a percentage of the total number of developed panicles. 0% meant that no diseased panicles were present; 100% meant that all the panicles were diseased. The fewer diseased panicles were formed, the more effective was the active compound.

The active compounds, the concentrations of the active compounds in the dressing, the amounts of dressing used and the number of diseased panicles can be seen from the following table:

TABLE 5

Seed dressing test/loose smut of barley

| Active compounds | Active compound concentration in the dressing in % by weight | Amount of dressing used in g/kg of seed | Number of smutted panicles, in % of the total panicles counted |
|---|---|---|---|
| Without dressing | — | — | 11.4 |
| (J) | 25 | 10 | 12.3 |
| (K) | 25 | 10 | 9.2 |
| (1) | 25 | 10 | 0.0 |
| (7) | 25 | 10 | 0.0 |

EXAMPLE 10

Fusicaladium test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18°–20° C. and at a relative atmospheric humidity of 100%.

The plants were then brought into a greenhouse for 14 days.

15 days after inoculation, the infection of the seedlings was determined. The ratings obtained were converted to percent infection. 0% meant no infection; 100% meant that the plants were completely infected.

The active compounds, the concentrations of the active compounds and the results can be seen from the following table:

TABLE 6

Fusicladium test (apple)/protective

| Active compound | Infection in % at an active compound concentration of | | |
|---|---|---|---|
|  | 0.025% | 0.01% | 0.0025% |
| (D) | 43 |  |  |
| (L) |  | 62 |  |
| (1) |  | 59 |  |
| (7) |  | 62 |  |
| (4) |  |  | 26 |
| (6) |  | 10 |  |

EXAMPLE 11

Uromyces test (bean rust)/protective
Solvent: 4.7 parts by weight of acetone
Emulsifier: 0.3 part by weight of alkylaryl polyglycol ether
Water: 95 parts by weight The amount of active compound required for the desired concentration of active compound in the spray liquor was mixed with the stated amount of the solvent and the concentrate was diluted with the stated amount of water which contained the stated additives.

Young bean plants, which were in the 2-leaved stage, were sprayed with the spray liquor until dripping wet. The plants remained in a greenhouse for 24 hours at 20°–22° C. and a relative atmospheric humidity of 70% in order to dry. They were then inoculated with an aqueous uredospore suspension of the causative organism of bean rust (*Uromyces phaseoli*) and incubated for 24 hours in a dark humidity chamber at 20°–22° C. and 100% relative atmospheric humidity.

The plants were then set up in a greenhouse under intensive illumination for 9 days at 20°–22° C. and a relative atmospheric humidity of 70–80%.

10 days after the inoculation, the infection of the plants was determined. The ratings obtained were converted to percent infection. 0% denoted no infection and 100% denoted that the plants were completely infected.

The active compounds, active compound concentrations and results can be seen from the following table:

TABLE 7

| | Uromyces test/protective | |
|---|---|---|
| | Infection in % of the infection of the untreated control at an active compound concentration (in %) of | |
| Active compound | 0.005% | 0.0025% |
| (L) | 59 | — |
| (1) | — | 46 |
| (7) | — | 12 |
| (4) | — | 54 |
| (8) | — | 29 |

EXAMPLE 12

Erysiphe test (cucumbers)/protective
Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of solvent and the concentrate was diluted with the stated amount of water containing the stated addition.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus Erysiphe cichoriacearum. The plants were subsequently placed in a greenhouse at 23°–24° C. and at a relative atmospheric humidity of about 75%.

After 12 days, the infection of the cucumber plants was determined. The assessment data were converted to percent infection. 0% meant no infection; 100% meant that the plants were totally infected.

The active compounds, the concentrations of the active compounds and the results can be seen from the following table:

TABLE 8

| | Erysiphe test (cucumbers)/protective | |
|---|---|---|
| Active compound | Infection in % at an active compound concentration of | |
| | 0.00031% | 0.00025% |
| (E) | 66 | — |
| (L) | 29 | — |
| (2) | — | 19 |
| (3) | — | 16 |

EXAMPLE 13

Pellicularia test
Solvent: 11.75 parts by weight of acetone
Dispersing agent: 0.75 part by weight of alkylaryl polyglycol ether
Water: 987.50 parts by weight
Other additives: - parts by weight The amount of active compound required for the desired concentration of active compound in the spray liquor was mixed with the stated amount of the solvent and of the dispersing agent and the concentrate was diluted with the stated amount of water.

2×30 rice plants about 2-4 weeks old were sprayed with the spray liquor until dripping wet. The plants remained in a greenhouse at temperatures of 22° to 24° C. and a relative atmospheric humidity of about 70% until they were dry. The plants were infected with a culture of Pellicularia sasakii grown on malt agar and were set up at 28° to 30° C. and 100% relative atmospheric humidity.

In the case of the plants infected with Pellicularia sasakii, the infection at the leaf sheaths after 5 to 8 days was determined, in relation to the untreated but infected control. The evaluation was made on a scale from 1 to 9. 1 denoted 100% action, 3 denoted good action, 5 denoted moderate action and 9 denoted no action.

The active compounds, the concentrations of the active compounds and the results can be seen from the table which follows.

TABLE 9

| | Pellicularia test |
|---|---|
| Active compound | Rating of infection at an active compound concentration of 0.025% |
| (M) | 9 |
| (1) | 3 |
| (8) | 5 |
| (3) | 3 |
| (6) | 3 |

It will be appreciated that the instant specification and examples are set forth by way of illustration and not limitation, and that various modifications and changes may be made without departing from the spirit and scope of the present invention.

What is claimed is:

1. A 4-phenoxy-4-(azol-1-yl)-butanoic acid derivative or a salt thereof, said derivative being of the formula $$\text{Zn} \diagdown \text{C}_6\text{H}_4 - \text{O} - \text{CH} - \text{A} - \overset{R^1}{\underset{R^2}{\text{C}}} - R$$

$$\overset{|}{\underset{N}{\text{N}}} \diagdown \overset{Y}{\underset{\parallel}{\phantom{N}}}$$

in which
A is —CO— or CH(OH)—,
Y is —CH= or —N=,
Z is halogen, alkyl with 1 to 4 carbon atoms, alkenyl with 2 to 4 carbon atoms, cycloalkyl with 5 to 7 carbon atoms, halogenoalkyl with 1 or 2 carbon atoms and 1 to 5 halogen atoms, alkoxy with 1 or 2 carbon atoms, alkylthio with 1 or 2 carbon atoms, alkoxycarbonyl with 1 to 5 carbon atoms in the alkoxy part, amino, cyano, nitro, or phenyl or phenoxy either of which may be substituted by halogen, amino, cyano, nitro or alkyl with 1 or 2 carbon atoms, or Z represents phenylalkyl with 1 or 2 carbon atoms in the alkyl part and which may be substituted phenyl part by halogen, nitro or cyano,
R is cyano, —CO—OR³ or —CO—NR⁴R⁵,
R¹ and R² each independently is alkyl with 1 to 4 carbon atoms, phenyl or phenyl substituted by halogen, alkyl with 1 or 2 carbon atoms or halogenoalkyl with 1 or 2 carbon atoms and 1 to 5 halogen atoms, or conjointly one tetramethylene or pentamethylene;
R³ is alkyl with 1 to 6 carbon atoms, $R^4$ is hydrogen, alkyl with 1 to 4 carbon atoms, phenyl or phenyl substituted by halogen, alkyl with 1 or 2 carbon atoms or halogenoalkyl with 1 or 2 carbon atoms and 1 to 5 halogen atoms, and $R^5$ is hydrogen or alkyl with 1 to 4 carbon atoms, and n is 0, 1, 2, 3, 4 or 5.

2. A compound according to claim 1, wherein such compound is 4-(4-chlorophenoxy)-2,2-dimethyl-3-keto-4-(1,2,4-triazol-1-yl)-butanoic acid ethyl ester of the formula

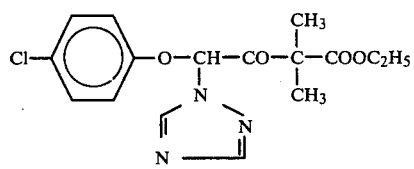

or a salt thereof.

3. A compound according to claim 1, wherein such compound is 4-(4-chlorophenoxy)-2,2-dimethyl-3-keto-4-(imidazol-1-yl)-butanoic acid ethyl ester of the formula

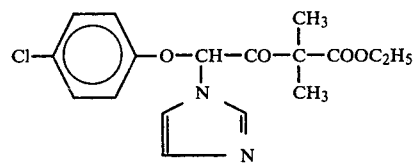

or a salt thereof.

4. A compound according to claim 1, wherein such compound is 4-(4-chlorophenoxy)-2,2-dimethyl-3-hydroxy-4-(imidazol-1-yl)-butanoic acid ethyl ester of the formula

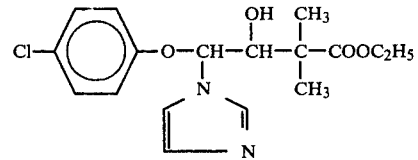

or a salt thereof.

5. A compound according to claim 1, wherein such compound is 4-(2,4-dichlorophenoxy)-2,2-dimethyl-3-keto-4-(imidazol-1-yl)-butanoic acid ethyl ester of the formula

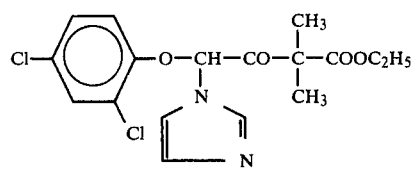

or a salt thereof.

6. A compound according to claim 1, wherein such compound is 4-(4-chlorophenoxy)-2,2-dimethyl-3-keto-4-1,2,4-triazol-1-yl)-butanoic acid ethyl ester of the formula

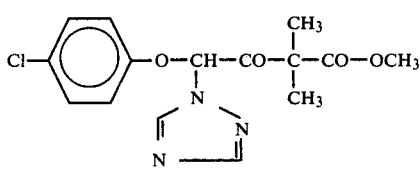

or a salt thereof.

7. A fungicidal composition containing as active ingredient a fungicidally effective amount of a compound according to claim 1 in admixture with a diluent.

8. A method of combating fungi which comprises applying to the fungi, or to a habitat thereof, a fungicidally effective amount of a compound according to claim 1.

9. The method according to claim 8 in which said compound is
4-(4-chlorophenoxy)-2,2-dimethyl-3-keto-4-(1,2,4-triazol-1-yl)-butanoic acid ethyl ester,
4-(4-chlorophenoxy)-2,2-dimethyl-3-keto-4-(imidazol-1-yl)-butanoic acid ethyl ester,
4-(4-chlorophenoxy)-2,2-dimethyl-3-hydroxy-4-(imidazol-1-yl)-butanoic acid ethyl ester,
4-(2,4-dichlorophenoxy)-2,2-dimethyl-3-keto-4-(imidazol-1-yl)-butanoic acid ethyl ester or
4-(4-chlorophenoxy)-2,2-dimethyl-3-keto-4-(1,2,4-triazol-1-yl)-butanoic acid methyl ester,
or a salt thereof.

10. The method according to claim 8, in which said compound is applied to a plant, seed or soil.

* * * * *